United States Patent
Huber et al.

(10) Patent No.: US 12,354,265 B2
(45) Date of Patent: Jul. 8, 2025

(54) MACHINE LEARNING BASED EVALUATION OF LATERAL FLOW TESTS

(71) Applicant: LIFTRIC GMBH, Mannheim (DE)

(72) Inventors: Jakob Huber, Limburgerhof (DE); Ben John, Hockenheim (DE); Thorsten Knoeller, Mannheim (DE)

(*) Notice: Subject to any disclaimer, the term of this patent is extended or adjusted under 35 U.S.C. 154(b) by 0 days.

(21) Appl. No.: 18/719,043

(22) PCT Filed: Dec. 10, 2022

(86) PCT No.: PCT/EP2022/085268
§ 371 (c)(1),
(2) Date: Jun. 12, 2024

(87) PCT Pub. No.: WO2023/110692
PCT Pub. Date: Jun. 22, 2023

(65) Prior Publication Data
US 2025/0054135 A1    Feb. 13, 2025

(30) Foreign Application Priority Data
Dec. 13, 2021  (EP) ..................................... 21213954

(51) Int. Cl.
*G06T 7/00* (2017.01)
*G01N 33/543* (2006.01)
(Continued)

(52) U.S. Cl.
CPC ..... *G06T 7/0012* (2013.01); *G01N 33/54388* (2021.08); *G06V 10/225* (2022.01);
(Continued)

(58) Field of Classification Search
CPC ......... G06T 7/0012; G06T 2207/10024; G06T 2207/20081; G06T 2207/20084;
(Continued)

(56) References Cited

U.S. PATENT DOCUMENTS 9,756,324 B1 * 9/2017 Flanagan ............... H04N 23/84
2013/0273528 A1 * 10/2013 Ehrenkranz ........ G01N 21/8483
435/7.9
(Continued)

OTHER PUBLICATIONS

International Search Report and Written Opinion for International Application No. PCT/EP2022/085268, mailing date of Feb. 13, 2023.
(Continued)

*Primary Examiner* — Van D Huynh
(74) *Attorney, Agent, or Firm* — Fresh IP PLC; Micah Gunn

(57) ABSTRACT

The present invention concerns computer-implemented methods for use in lateral flow test evaluation. One embodiment of such a method comprises obtaining, preferably by a mobile electronic device (110), a digital image (202) that depicts at least one test cassette (100), wherein the test cassette (100) comprises at least one viewport (102) and wherein the viewport (102) comprises at least one test indicator (104). The method may comprise performing, preferably by the mobile electronic device (110), an image segmentation step (204) to recognize at least one test indicator (104) depicted in the digital image (202), and performing an evaluation step (206) for producing at least one evaluation result (208) based, at least in part, on the recognized at least one test indicator (104). The image segmentation step (204) may comprise generating at least one object marker (306, 406, 506), in particular at least one mask and/or bounding box, based on a downscaled version of the obtained digital image (202) and applying the at least one object marker (306, 406, 506) to the obtained digital image (202) or to a part thereof.

10 Claims, 13 Drawing Sheets

(51) Int. Cl.
  *G06V 10/22* (2022.01)
  *G06V 10/26* (2022.01)
  *G06V 10/32* (2022.01)
  *G06V 10/77* (2022.01)
  *G06V 10/82* (2022.01)

(52) U.S. Cl.
  CPC .............. *G06V 10/26* (2022.01); *G06V 10/32* (2022.01); *G06V 10/77* (2022.01); *G06V 10/82* (2022.01); *G06T 2207/10024* (2013.01); *G06T 2207/20081* (2013.01); *G06T 2207/20084* (2013.01); *G06V 2201/03* (2022.01)

(58) Field of Classification Search
  CPC ........... G01N 33/54388; G06V 10/225; G06V 10/26; G06V 10/32; G06V 10/77; G06V 10/82; G06V 2201/03; G06V 10/17; G06V 10/25
  See application file for complete search history.

(56) References Cited

U.S. PATENT DOCUMENTS

| | | | | |
|---|---|---|---|---|
| 2014/0065647 | A1* | 3/2014 | Mamenta | G01N 21/274 435/7.92 |
| 2015/0308961 | A1* | 10/2015 | Burg | G01N 21/78 |
| 2018/0293350 | A1* | 10/2018 | Dimov | G16H 50/20 |
| 2021/0172945 | A1* | 6/2021 | Armbruster | G01N 21/8483 |
| 2021/0327056 | A1* | 10/2021 | Needham | G06T 7/30 |
| 2022/0084659 | A1* | 3/2022 | Rowe | G06V 10/993 |
| 2023/0013247 | A1* | 1/2023 | Armbruster | G06T 7/80 |
| 2023/0146924 | A1* | 5/2023 | Kumar | G16H 30/40 382/128 |
| 2023/0274538 | A1* | 8/2023 | Sia | G06V 10/82 382/155 |
| 2023/0296600 | A1* | 9/2023 | Rowe | G06V 10/56 435/7.92 |

OTHER PUBLICATIONS

Siddarth et al. "Adaptable Automated Interpretation of Rapid Diagnostic Tests Using Few-Shot Learning", medRxiv, Jun. 25, 2021 (Jun. 25, 2021), XP055901171, DOI: 10.1101/2021.06.23. 21258927 Retrieved from the Internet: URL:https://www.medrxiv.org/content/10.110 1/2021.06.23.21258927v1.full.pdf.

Qi et al. "Deep Learning on chromatographic data for Segmentation and Sensitive Analysis", Journal of Chromatography A, Elsevier, Amsterdam, NL, vol. 1634, Nov. 5, 2020 (Nov. 5, 2020), XP086377499, ISSN: 0021-9673, DOI: 10.1016/J.CHROMA.2020.461680.

Mendels et al. "Using artificial intelligence to improve COVID-19 rapid diagnostic test result interpretation", Proceedings of the National Academy of Sciences, vol. 118, No. 12, Mar. 5, 2021 (Mar. 5, 2021), XP055900914, ISSN: 0027-8424, DOI: 10.1073/pnas.2019893118.

Search Report for EP 21213954.7-1207, dated May 24, 2022.

* cited by examiner

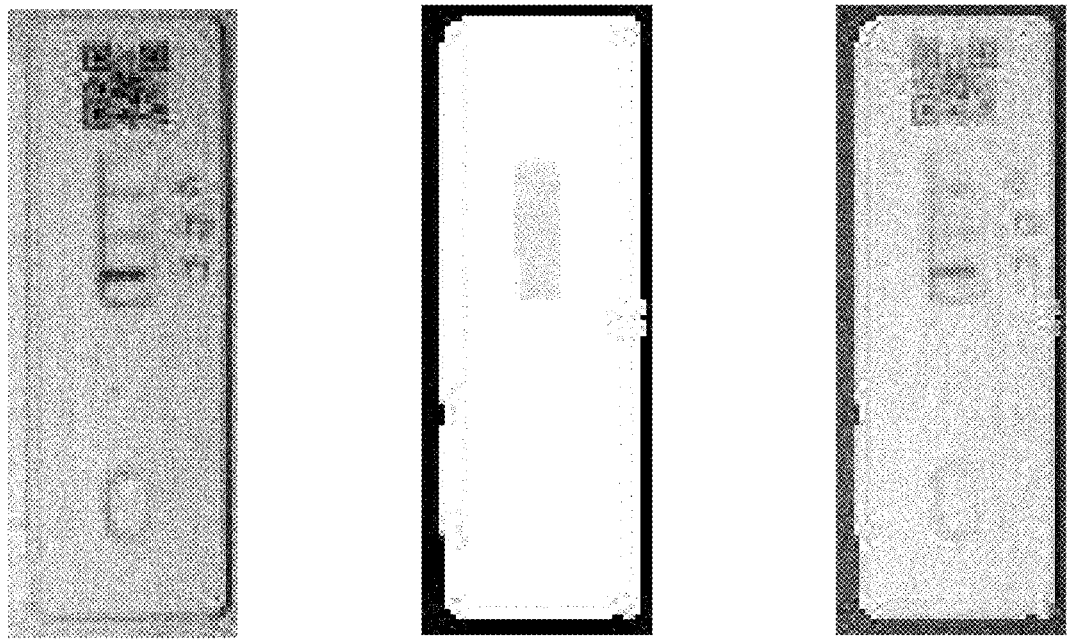
FIG. 8B
FIG. 8C
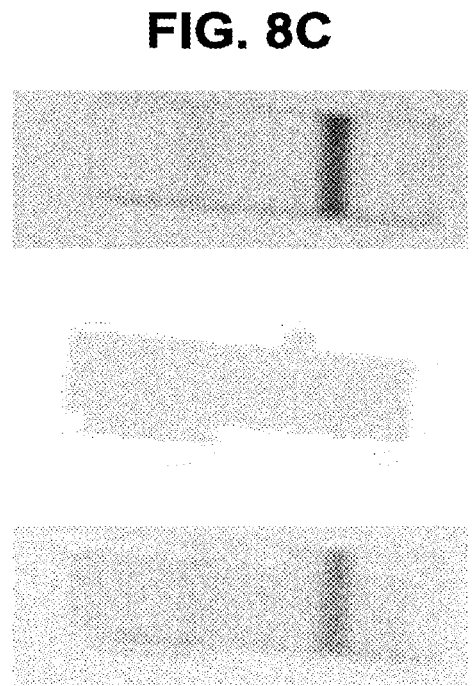

MACHINE LEARNING BASED EVALUATION OF LATERAL FLOW TESTS

TECHNICAL FIELD

The present invention generally concerns the field of lateral flow assay analysis, and in particular a machine-learning technique for quantitative analysis of lateral flow assays.

BACKGROUND

Lateral flow assays (LFAs) are nowadays widely used. LFAs, also known as lateral flow immunochromatographic assays, lateral flow tests (LFTs) or rapid tests, are relatively simple diagnostic devices used for confirming the presence or absence of a target analyte, such as pathogens or biomarkers in humans or animals. The lateral flow assays are typically housed in test cassettes having at least one sample drop and one or more viewports that provide visibility to the test band(s) and control band(s) of each assay. Early versions of LFTs were mostly qualitative assays, but more recent improvements in the technology also allow for a quantitative analysis of the test results.

Three typical examples of an LFA device are shown in FIG. 1A. As can be seen, the LFA devices comprise a test cassette 100 with an area where a fluid sample can be applied (labelled "S" on the cassette on the upper left-hand side of FIG. 1A). The two test cassettes 100 on the top of FIG. 1A further comprise a viewport 102 with one or more test lines 104. The cassette 100 on the upper left-hand side of FIG. 1A includes only a single test line 104 labelled "T", whereas the cassette 100 on the upper right-hand side of FIG. 1A includes two test lines 104 labelled "T1" and "T2". Both cassettes 100 also include a control line 106 labelled "C". The test cassette 100 on the bottom of FIG. 1A is an example of a multiplex test with two viewports 102. The test line(s) 104 and the control line 106 are sometimes also referred to as "signals", while the control line 106 may also be referred to as "C band" or "control indicator" and the test line(s) 104 may be referred to as "T band(s)" or "test indicator(s)".

The simplest way of evaluating a test result produced by an LFA is by visual inspection of the viewport 102 to identify the presence of the test line(s) 104. More recently, however, also automated evaluation techniques have been developed, which typically include an automated optical analysis of the LFA 100 with an immunochromatographic reader or another device.

FIG. 1B shows an example where a smartphone 110 is used to take a picture of an LFA cassette 100, which can then be analyzed in an automated fashion. A corresponding system for analyzing quantitative lateral flow chromatography is disclosed in US 2021/0172945 A1. The disclosed system aims at compensating the oftentimes insufficient image quality caused by the variety of camera hardware used in smartphones by automatically determining the distance between the camera and the LFA cassette as well as the measure of light in the region of interest of the LFA prior to the retrieval of image data. The disclosed system primarily focuses on metrics for evaluating the quality of the captured image.

Typically, automated LFA evaluation techniques require a fiducial marker (e.g., a QR code or EAN barcode) or other visual feature to detect the test cassette (see the markers 108 in FIG. 1A). However, such marker-based devices suffer from several drawbacks. Firstly, they are costly in terms of manufacturing because the marker needs to be printed onto the device, which increases the complexity of the manufacturing process, and even with sophisticated printing techniques the quality of the markers is oftentimes washed out or the marker position is tilted. Secondly, the visual markers are relatively vulnerable to the tilt or angle of the test cassette relative to the camera because the visual marker is needed as the origin of the image recognition and used as an anchor for finding the viewport in the digital image. Thirdly, the results of the signal analysis greatly vary depending on the lighting conditions. Finally, the automated evaluation techniques must be adapted extensively for each individual type of test cassette (note that FIG. 1A shows only three possible types, but the layouts of available test cassettes vary greatly in reality).

A further drawback of most existing solutions is that only one viewport at a time can be analyzed. Accordingly, it is not possible to evaluate multiple test cassettes per image, let alone so-called multiplex tests with multiple viewports on one test cassette, such as the one shown in FIG. 1A (bottom). Additionally, many existing solutions require a so-called calibration card to adjust the camera. Further, even small manufacturing deviations are harmful to the test analysis, e.g., when the test line(s) or control line are slightly moved towards the housing so that their positions vary from test cassette to test cassette. Furthermore, many existing techniques require extensive processing power and computing resources to perform the image recognition and analysis.

Moreover, what is desired in certain use cases is a defined and reproducible value of the control line, i.e., the C band, for normalizing the intensity value of the test line(s), i.e., the T band(s), the final signal then being $(T1+ \ldots +Tn)/C$.

It is therefore a problem underlying the invention to provide an improved automated LFA evaluation technique which overcomes the above-mentioned disadvantages of the prior art at least in part.

SUMMARY

One embodiment of the invention provides a computer-implemented method for lateral flow test evaluation or use in such evaluation. The method may comprise a step of obtaining, preferably by a mobile electronic device, a digital image that depicts at least one test cassette. Accordingly, the method may operate on an input image that contains only one test cassette, or it may be used to process images that contain multiple test cassettes, which improves the efficiency of the test evaluation process. Obtaining the digital image may comprise capturing the digital image with a camera of the mobile electronic device, which leads to a particularly convenient and efficient evaluation process because essentially the entire process can be performed using just a mobile device, such as a smartphone. However, it is also possible that the digital image is received by the mobile device from other sources, e.g., the image may have been taken with a camera external to the mobile device and transferred to the mobile device in any practical manner. Alternatively, the concepts disclosed herein, or at least parts thereof, may also be performed on a computing system separate to the mobile electronic device.

A test cassette may comprise a viewport (or multiple viewports in case of a multiplex test). A viewport may comprise at least one test indicator (typically one or two test indicators) and, optionally, a control indicator.

The method may comprise performing, preferably by the mobile electronic device, an image segmentation step to recognize at least one test indicator depicted in the digital image. The method may further comprise performing, preferably by the mobile electronic device, an evaluation step for producing at least one evaluation result based, at least in part, on the recognized at least one test indicator.

The image segmentation step may comprise generating at least one object marker based on a downscaled version of the obtained digital image and applying the at least one object marker to the obtained digital image or to a part thereof.

Accordingly, embodiments of the invention provide a unique solution for analyzing any lateral flow assay in a quantitative way in multiple different environments in a particularly efficient manner. In particular, the image data to be processed is in the above-described aspect first reduced, the corresponding object marker(s) is/are created based on the reduced image data, and then the object marker(s) is/are applied on the original image data. This makes it possible to perform fast and robust image processing with reduced processing power and storage capacity. In other words, the image processing operates largely on downscaled images, which allows for component recognition without a relevant loss of accuracy and at the same time significantly saves processing resources and thus enables a real-time processing on mobile devices. The (upscaled) object marker of an identified component may then be used to cut out the corresponding element in the original image material, rather than the downscaled image material, which provides more details to the subsequent analysis. Therefore, in summary, this aspect advantageously differentiates embodiments of the invention from the prior art which either perform the image analysis on downscaled images (and which are thus less precise) or do not downscale images (and thus result in large models).

The at least one object marker may be at least one mask, bounding box, and/or more generally any means for marking a given instance of an object in an image. As will be explained in more detail below, a mask may provide for a particularly simple mechanism to mark objects, whereas using bounding boxes may be preferred e.g., in scenarios where the input image depicts a plurality of test cassettes, in which two test cassettes may be arranged closely together in the image.

The method may further comprise, preferably as part of the image segmentation step, a test cassette extraction step, a viewport extraction step, and/or a signal detection step.

In one aspect of the method, the test cassette extraction step may comprise the steps of generating a downscaled digital image from the obtained digital image, generating, based on the downscaled digital image, a first object marker associated with a test cassette depicted in the obtained digital image, preferably one first object marker for each test cassette depicted in the obtained digital image, and extracting, using the first object marker, a test cassette image from the obtained digital image, preferably one test cassette image for each test cassette depicted in the obtained digital image.

The viewport extraction step may be based at least in part on the extracted test cassette image. The viewport extraction step may comprise the steps of generating a downscaled test cassette image from at least part of the obtained digital image, preferably from the test cassette image, generating, based on the downscaled test cassette image, a second object marker associated with a viewport depicted in the obtained digital image, and extracting, using the second object marker, a viewport image from at least part of the obtained digital image, preferably from the test cassette image.

The signal detection step may be based at least in part on the extracted viewport image. The signal detection step may comprise the steps of generating a downscaled viewport image from at least part of the obtained digital image, preferably from the test cassette image, more preferably from the viewport image, and generating, based on the downscaled viewport image, a third object marker associated with at least one test indicator depicted in the obtained digital image. The evaluation step may be based at least in part on the third object marker.

Accordingly, an entire image processing pipeline may be established for first extracting the test cassette from the overall image, then extracting the viewport, and then extracting the one or more test indicators as a basis for further analysis. Comparative tests have shown that the signal analysis accuracy is significantly improved, assuming 10% coefficient of variance in traditional techniques as compared to approx. 3 to 7% with embodiments of the invention.

Generating the at least one object marker may comprise processing the respective downscaled image with at least one segmentation machine-learning model. For example, generating the first object marker may comprise processing the obtained digital image with a first segmentation machine-learning model. Generating the second object marker may comprise processing the downscaled test cassette image with a second segmentation machine-learning model. Generating the third object marker may comprise processing the downscaled viewport image with a third segmentation machine-learning model.

Accordingly, machine-learning techniques, also commonly referred to as artificial intelligence (AI) may be used to provide a particularly powerful test evaluation. In the above-described aspect, the AI is trained how a typical test cassette looks like and which components it includes, in particular the viewport, the test indicator(s) and, optionally, a control indicator of the at least one test cassette.

Preferably, there is provided a separate machine-learning model for each object marker, i.e., the first segmentation machine-learning model, the second segmentation machine-learning model and the third segmentation machine learning model may be separate machine-learning models. Accordingly, this aspect provides a modular machine-learning technique that is particularly adaptable. For example, when one of several manufacturers of test cassettes puts a new type of test cassette onto the market which has new unique properties but the same type of viewport as other types of test cassettes, it is possible to retrain the first machine-learning model, i.e., the one for extracting the test cassette, while leaving the other machine-learning models untouched.

The evaluation step may comprise using a prediction machine-learning model to generate values for the at least one test indicator, and optionally, a control indicator of the at least one test cassette. This enables an accurate quantitative evaluation of the lateral flow test.

The downscaled digital image may be downscaled by a predefined factor, in particular a factor selected from the range of 5 to 15, more preferably from the range of 8 to 12, or from the range of 2 to 8, more preferably from the range of 4 to 6. Most preferably, the downscaled digital image is downscaled by a factor of 10 or 5 relative to the obtained digital image, which the inventors have found to be an optimal trade-off between image size reduction and image recognition quality. In particular, a factor of approximately 10, resulting in rather small-sized downscaled images, has been found to still yield acceptable results when using a masks as object marker, whereas a factor of approximately 5 has been found to yield good results when using a bounding box as object marker because (rotated) bounding boxes may need more pixel information.

In one exemplary implementation, the size of the obtained digital image is 1280×720 pixels and the size of the downscaled digital image is 128×72 pixels (when using a downscaling factor 10) or 256×144 pixels (when using a downscaling factor of 5). The size of the downscaled test cassette image may be 40×120 pixels or 80×240 pixels. The size of the downscaled viewport image may be 80×24 pixels or 160×48 pixels or 128×32 pixels. The inventors have found that these image sizes lend themselves to a sufficiently accurate image processing while ensuring that the image data is as small as possible. Generally speaking, a larger image size may lead to better segmentation results but may decrease the runtime performance. The image sizes 128×72 and 256×144 have been found to work well and to represent a reasonable trade-off between accuracy and runtime. However, the principles of the invention are not bound to these specific sizes and scaling factors, and other sizes, as well as corresponding scaling factors, may be used as applicable, such as 64×36, 128×72, 256×144, 512×288, 1024×576, 1280×720.

The downscaled digital image may adhere to an RGB color model, the downscaled test cassette image may adhere to an RGB color model and/or the downscaled viewport image may adhere to a Lab color model. The RGB color model comprises an established color space that is particularly suitable for machine learning, in particular deep learning. The Lab color model comprises a dedicated channel for the brightness, which is useful for the test indicator evaluation, as will be explained in more detail further below.

The method may further comprise performing at least one sanity check on the extracted test cassette image, e.g., as part of the test cassette extraction step. The method may further comprise performing at least one sanity check on the extracted viewport image, e.g., as part of the viewport extraction step. The method may further comprise validating the downscaled test cassette image, preferably using a test cassette validation machine-learning model, e.g., as part of the viewport extraction step. The method may further comprise validating the downscaled viewport image, preferably using a viewport validation machine-learning model, e.g., as part of the test indicator extraction step.

Accordingly, the extracted images may be subjected to a validation to ensure that they are suitable for the next step in the processing pipeline.

The first segmentation machine-learning model, the second segmentation machine-learning model, the third segmentation machine-learning model, the prediction machine-learning model, the test cassette validation machine-learning model and/or the viewport validation machine-learning model may comprise an artificial neural network, in particular a convolutional neural network (CNN). In general, the method preferably uses models that enable real-time or near real-time image processing on mobile devices. In one implementation, all models may be based on CNNs, as they are particularly suitable for image analysis.

Different types of CNNs may be used based on the task at hand. For instance, the ResNet models were designed for image classification but can also used as backbone (feature extractor) for other tasks. In one aspect of the invention, the at least one segmentation model, i.e., the models that predict object markers (such as masks or bounding boxes), is/are based on or comprise a U-Net (e.g., as disclosed in "U-Net: Convolutional Networks for Biomedical Image Segmentation" by O. Ronneberger et al. in N. Navab et al. (Eds.): MICCAI 2015, Part III, LNCS 9351, pp. 234-241, 2015; DOI: 10.1007/978-3-319-24574-4_28; https://link.springer.com/content/pdf/10.1007/978-3-319-24574-4_28.pdf).

In one aspect of the invention, the validation and/or regression model(s) is/are based on or comprise one or more building blocks of MobileNets, which are particularly suitable for image analysis (classification, etc.) on mobile devices (e.g., as disclosed in "MobileNetV2: Inverted Residuals and Linear Bottlenecks" by M. Sandler et al. in IEEE Conference on Computer Vision and Pattern Recognition (CVPR), 2018, pp. 4510-4520; arXiv:1801.04381; https://arxiv.org/abs/1801.04381). MobileNets typically serve the same purpose as ResNets but can be much smaller.

Yet another implementation of the instance segmentation models, in particular for predicting bounding boxes, may be based on Yolo models (e.g., as disclosed in "You Only Look Once: Unified, Real-Time Object Detection" by J. Redmon et al.; arXiv:1506.02640; https://arxiv.org/abs/1506.02640).

The mobile electronic device may be a handheld device, in particular a handheld consumer device such as a smartphone or tablet computer. Accordingly, it is made possible to perform the entire or substantially the entire image processing on a device with limited processing power and storage capacity.

The invention also concerns a computer-implemented method for training a machine-learning model for use in any one of the methods disclosed herein. The invention also concerns a machine-learning model or configuration of machine-learning models, configured for being used in a method for lateral flow test evaluation in accordance with any of the aspects disclosed herein.

Also, a data processing apparatus is provided, the apparatus comprising means for carrying out any one of the methods disclosed herein.

Lastly, the invention also provides a computer program comprising instructions which, when the program is executed by a computer, cause the computer to carry out any one of the methods disclosed herein.

BRIEF DESCRIPTION OF THE DRAWINGS

The disclosure may be better understood by reference to the following drawings:

FIG. 8B: An exemplary test cassette image and a corresponding viewport mask in accordance with embodiments of the invention FIG. 8C: An exemplary viewport image and a corresponding signal mask in accordance with embodiments of the invention FIG. 9A,B: Exemplary input images with a single and multiple test cassettes and corresponding masks and bounding boxes

DESCRIPTION OF PREFERRED EMBODIMENTS

Embodiments of the invention concern a machine-learning based lateral flow assay (LFA) evaluation algorithm in which the machine-learning model is trained how a typical test cassette looks like and which components it includes (test cassette, viewport, bands). Consequently, many test devices can be recognized without or with only minimal additional effort, as long as they are sufficiently similar to the test devices with which the model has been trained. To ensure fast, robust and at the same time small-sized models for the algorithm, the image material is reduced, and the resulting mask, bounding box or object marker is then applied on the original image material.

This way, embodiments of the invention provide an approach for the quantitative and qualitative analysis of images (i.e., single images or sequences of images) depicting one or more lateral flow assay (LFA) tests. Each image may depict an arbitrary number of test cassettes, e.g., 0 to 100. Embodiments of the invention may detect unique instances of test cassettes and their components within an image to evaluate the signal values.

Process Overview

Figure 1A:
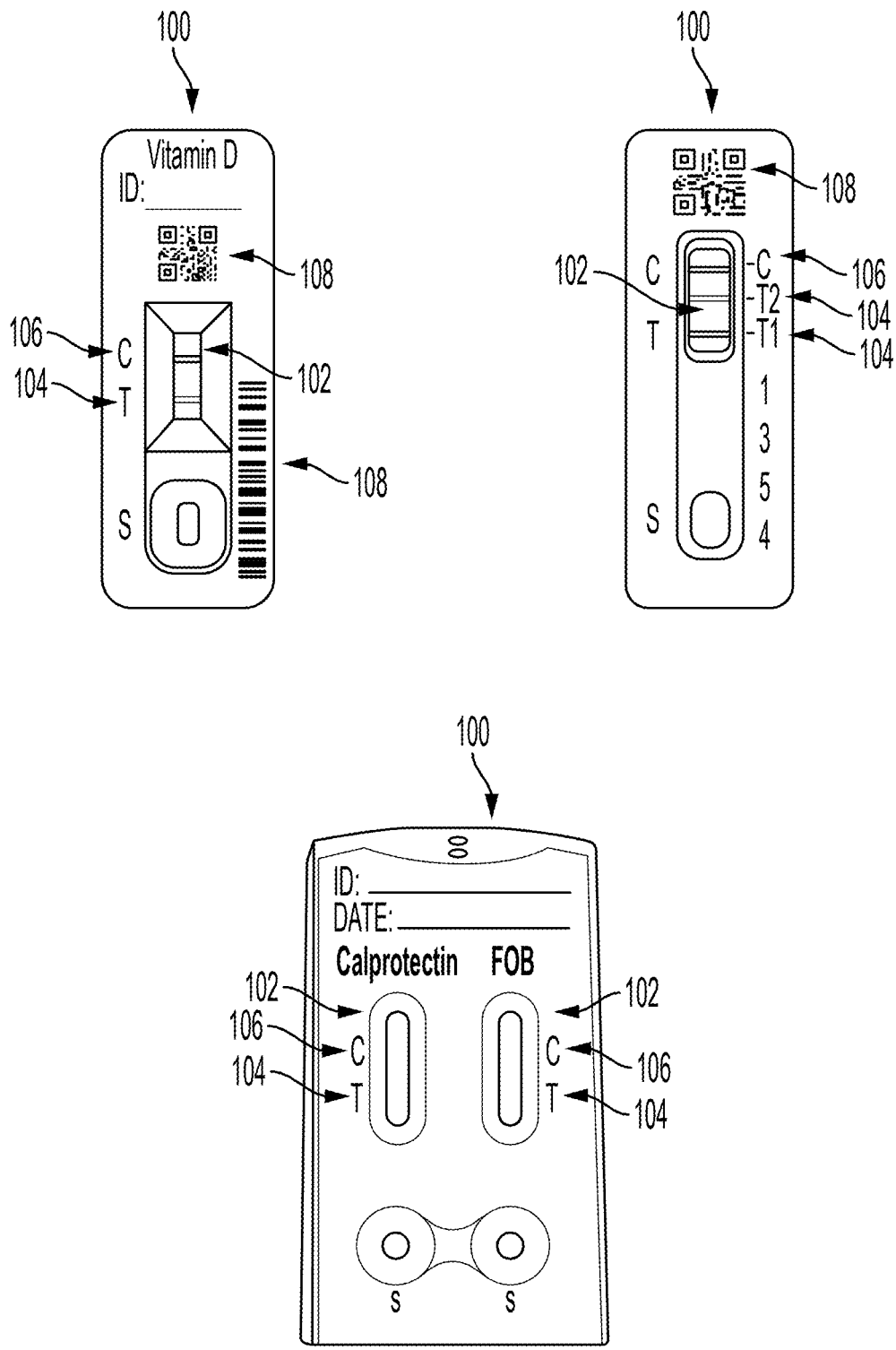
FIG. 1A: Exemplary LFA test cassettes
Figure 2:
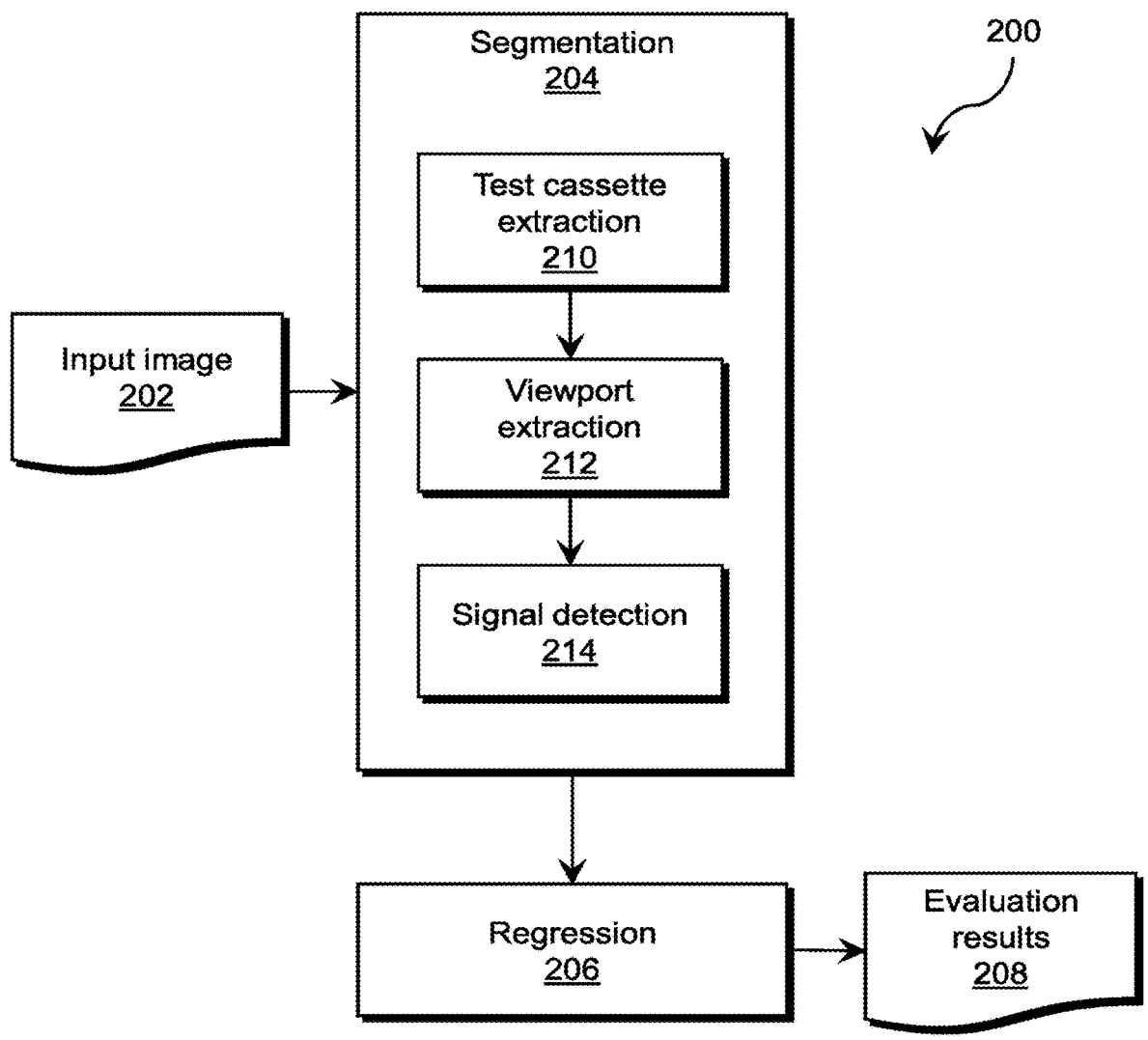
FIG. 2: A flowchart illustrating a high-level process for evaluating an LFA test in accordance with embodiments of the invention
Figure 8A:
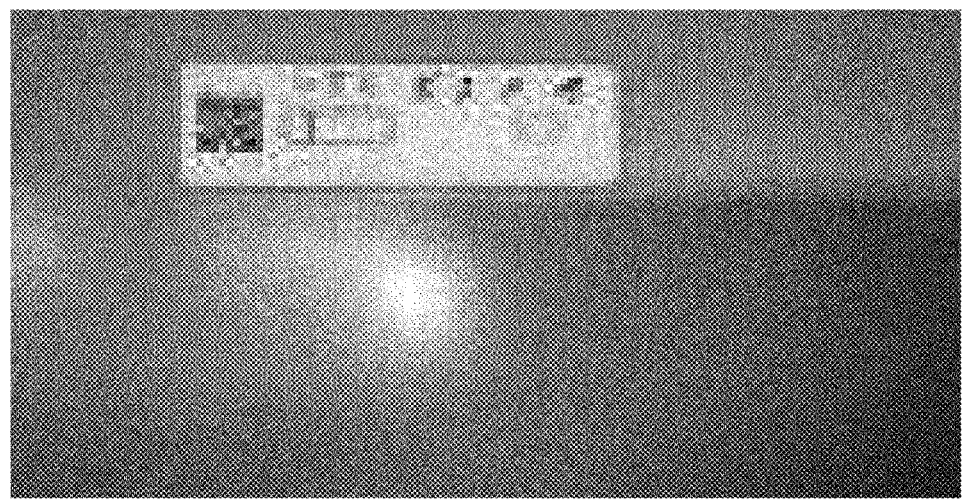
FIG. 8A: An exemplary input image and a corresponding test cassette mask in accordance with embodiments of the invention
Figure 8A:
Figure 8A:
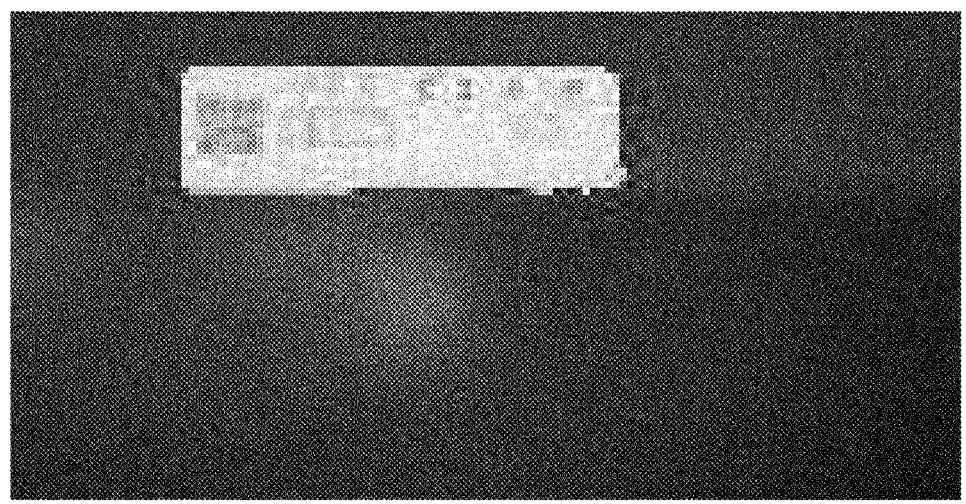

FIG. 2 shows a flowchart of a high-level process 200 according to an embodiment of the invention. As can be seen, an input image 202, also referred to as initial digital image, serves as the input for the overall process 200. The input image 202 may be a digital image captured by a camera of an electronic device such as a smartphone 110. The input image 202 depicts a test cassette 100, such as one of the examples shown in FIG. 1A. An example of an input image 202 is shown in FIG. 8A (at the top). Although embodiments of the invention will be explained mainly in connection with input images depicting only a single test cassette 100, the principles underlying the explained embodiments may be similarly applied to images with multiple test cassettes 100. Furthermore, embodiments of the invention may be configured to process a series of input images 202, although only "an" input image 202 is mentioned herein for simplicity.

The illustrated embodiment of the process 200 in FIG. 2 includes a segmentation phase 204, the primary purpose of which is to detect test instances and their components, and a regression phase 206 (also referred to as evaluation phase), the primary purpose of which is to analyze the signal values of each LFA, and ultimately produce one or more evaluation results 208. The overall objective of the process 200 is to predict one or more signals associated with the test cassette 100, in particular the direct signals "T" for a test cassette 100 with only one test indicator 104 (see the upper left-hand example in FIG. 1A; note that "T" may also be labelled "T1" in the following), "T1" and "T2" for a test cassette 100 with two test indicators 104 (see the upper right-hand example in FIG. 1A) and/or "C", i.e. the control indicator 106, as well as one or more indirect signals, including ratios such as T1/C and T2/C.

Certain embodiments of the invention allow running the process 200 on a device with limited processing resources and storage capability, in particular on a conventional smartphone (e.g., under the Android and/or iOS operating systems) and may be able to process images in real-time, i.e. with more than 10 FPS. This way, a real-time, or near real-time, test analysis on mobile devices having limited computational power, e.g., smartphones, is made possible. It shall be appreciated that the embodiments disclosed herein may also execute on other devices.

Referring again to FIG. 2, the primary purpose of the segmentation phase 204 of the process 200 is the detection of test cassettes 100 and their components in the input image 202. In particular, embodiments of the invention provide a precise excerpt of the viewport 102, or each viewport 102 in the case of multiplex tests or multiple test cassettes in the image, including the detection of the signal bands. To obtain the viewport excerpts, each image may traverse a pipeline that includes, in the illustrated embodiment, a test cassette extraction step 210, a viewport extraction step 212 and a signal detection step 214. It shall be appreciated that other embodiments of the invention may include only a subset of these steps and/or phases as needed for the particular application. Accordingly, it is possible in certain embodiments of the invention to condense the image segmentation pipeline 204 if a specific application scenario allows it. For example, if the input images 202 contain only one test cassette 100, it may be possible to directly extract the viewport 102.

In one embodiment of the invention, the process 200 and the corresponding analysis of the test cassette(s) 100 that is/are depicted in the input image(s) 202 is performed using machine-learning models. In certain embodiments, the segmentation and/or validation of instances is done using convolutional neural networks (CNNs), which are artificial neural networks (ANNs) that are primarily used for computer vision tasks (e.g., image classification, object detection, segmentation, etc.). In some embodiments, two distinct approaches for instance segmentation based on CNNs are considered, namely the prediction of segmentation masks and the prediction of rotated bounding boxes, both of which will be explained in more detail further below. In some embodiments, the result of both segmentation approaches is processed by validation models and may also be subject to additional sanity checks, as will also be explained in more detail.

In certain embodiments, different machine-learning models are used for the individual steps of the image segmentation pipeline 204. In one embodiment, the test cassette extraction 210 involves a first model and serves for recognizing the test cassette 100 in the input image 202, for cutting out the test cassette 100 from the overall image 202, and optionally, for validating the recognized test cassette 100. Using a second model, the viewport extraction 212 serves for recognizing and cutting out the viewport 102, and optionally, for validating the recognized viewport 102. Using a third model, the signal detection 214 serves for recognizing the test line(s) 104 and/or control line 106 (which may also be referred to as "signals" or "bands"), creating a corresponding object marker, such as a mask, and optionally, for validating the recognized bands. Using separate machine-learning models for each, or at least some of the phases of the process 200 creates a particularly modular, flexible and adaptable technique, because changes to a particular model (e.g., a re-training) have minimal impact on the other models, and the models may even be exchanged or updated independently. For example, when a new type of test cassette 100 is put on the market, the shape of its housing may differ considerably from existing test cassettes 100 while the viewport 102 is the same or very similar. In this scenario, only the machine-learning model for the test cassette extraction must be updated, while the machine-learning model for the viewport extraction may remain unchanged.

Besides the above-explained modularity, the image processing pipeline 204 of certain embodiments of the invention, in particular that depicted in FIG. 2, may provide a number of further important technical advantages:

Quality: As mentioned, the detection and extraction of test cassette instances 100 generally comprises three steps (test cassette, viewports, signals). After each step, sanity and/or plausibility checks may be performed to ensure a high quality of the segmented objects, as will be explained in more detail further below. If a check fails, the processing pipeline may be aborted and the current image (e.g., image of a test cassette) may be discarded. Hence, only accurately detected viewports are passed to the regression module.

Runtime: As each step focuses on a specific aspect (e.g., test cassette, viewport, signals) it is possible to perform the operations on images having a lower but still sufficient resolution. In typical images, the test cassettes cover only 10% to 60% of the pixels while the remaining pixels can be classified as background. Hence, by detecting and extracting higher level objects, the succeeding phases contain a higher percentage of relevant pixels. Operating on images having lower resolutions does not affect the quality of the segmented entity as embodiments of the invention upscale the result of the segmentation algorithm to the initial resolution. Moreover, a pixel-perfect segmentation result is normally only required for the final segmentation step, i.e., the detection of signal bands within a viewport. It is also possible to employ smaller and faster models as each model focuses only on a certain part of the image, e.g., detecting a test cassette. Finally, if one step fails it is possible to abort the processing pipeline and discard the image of the processing branch.

For the prediction of object markers in the image segmentation pipeline 204, certain embodiments of the invention rely on semantic segmentation models to identify test cassettes 100 and their components in the images 202. Semantic segmentation models may be used for pixel-level classification, i.e., each pixel is assigned to a specific class. In embodiments of the invention, the following classes (labels) representing different parts of a LFA test 100 may be considered, or any subset thereof:

1. class 0: background
2. class 1: test cassette
3. class 2: viewport
4. class 3: signal: C (control band)
5. class 4: signal: T1 (test band)
6. class 5: signal: T2 (test band)

In a typical LFA test, the viewport 102 is part of the test cassette 100 and the test bands (signals) 104, 106 are part of the viewport 102. Depending on the granularity of the segmentation step, pixels belonging to a lower-level class may be assigned to a higher-level class. For example, the first segmentation model used for the text cassette extraction 201 may distinguish only between background and test cassette pixels.

The segmentation models may predict the probability distribution over the target classes for each pixel. To assign each pixel to a class, two techniques may be used in embodiments of the invention. Either a threshold may be applied to obtain a binary image (mask) or each pixel may be assigned to the class having the highest probability. In one embodiment, the former approach is used for the first segmentation step 210 (i.e., text cassette detection) and the latter approach is used for the remaining segmentation steps 212, 214.

For the test cassette segmentation 210 and the viewport segmentation 212, certain embodiments use the predicted segmentation masks to detect and segment instances. For this purpose, a standard computer vision algorithm may be used to find connected components (see, e.g., C. Grana et al., Optimized block-based connected components labeling with decision trees. IEEE Transactions on Image Processing, 19(6):1596-1609, 2010) which match the class of interest. Subsequently, a rotated rectangle of the minimum area enclosing each connected component may be computed to extract each instance.

The third segmentation step 214 is concerned with the segmentation of the signal bands (e.g., C, T1, T2). In some embodiment, the predicted probability distributions are part of the input of the regression model 206. However, it is also possible to obtain a mask or masks which can be used to determine the color values (e.g., signal values) by taking the median (mean) value of pixels belonging to a certain mask.

In principle, any semantic segmentation (e.g., J. Long et al., Fully convolutional networks for semantic segmentation. In Proceedings of the IEEE conference on computer vision and pattern recognition, pages 3431-3440, 2015; or L. Chen et al., Deeplab: Semantic image segmentation with deep convolutional nets, atrous convolution, and fully connected crfs. IEEE transactions on pattern analysis and machine intelligence, 40(4):834-848, 2017) may be used in the different segmentation steps according to embodiments of the invention. In certain embodiments, the inventors have found, however, that adaptions of a U-Net architecture (see, e.g., O. Ronneberger et al., U-net: Convolutional networks for biomedical image segmentation. In International Conference on Medical image computing and computer-assisted intervention, pages 234-241. Springer, 2015) are particularly suitable, as this allows real-time processing and accurate segmentation results.

In the following, each of the phases/steps of the process 200 of FIG. 2 will be explained in more detail with reference to FIGS. 3 to 7.

Test Cassette Extraction

Figure 3:
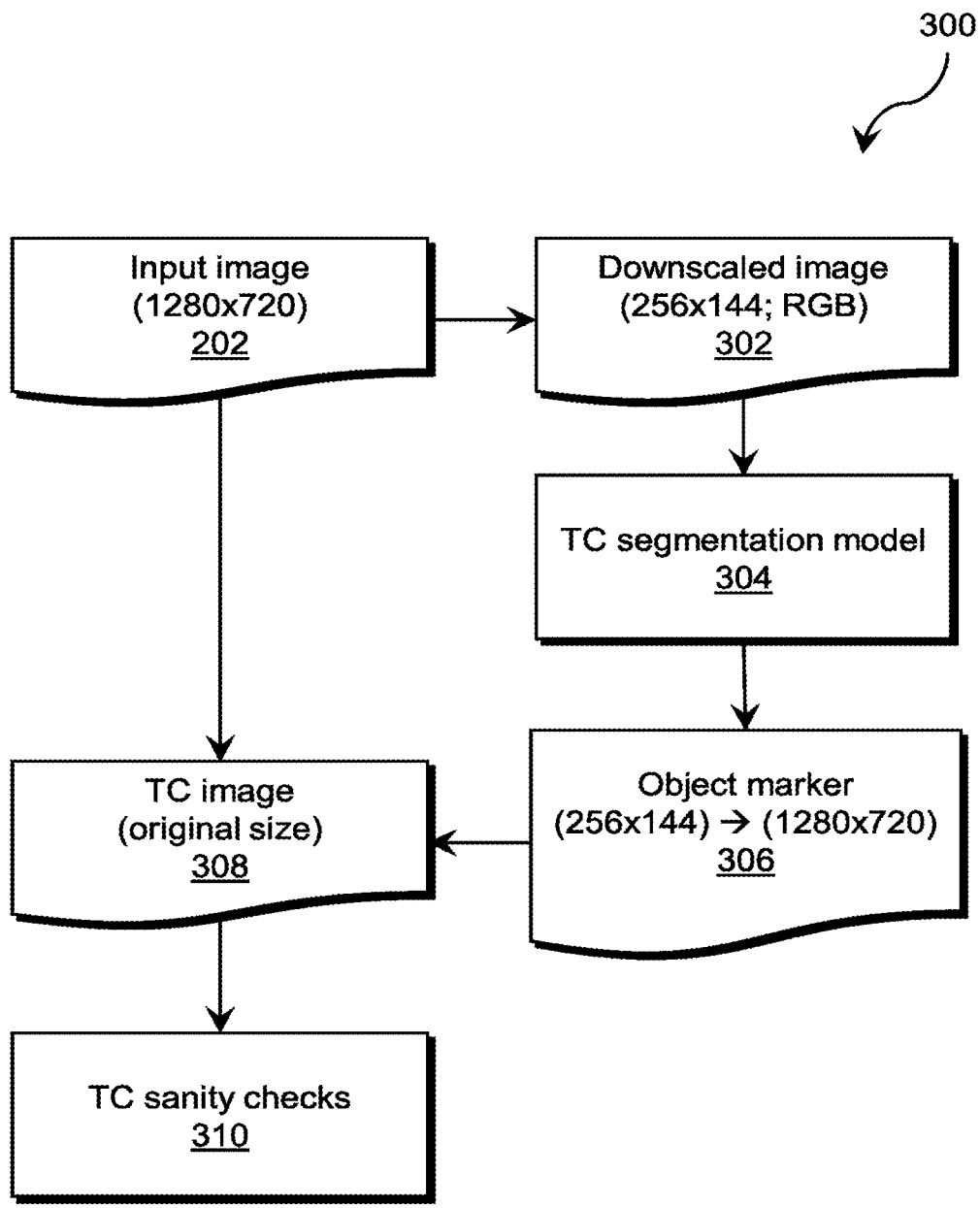
FIG. 3: A flowchart illustrating a test cassette extraction process in accordance with embodiments of the invention

FIG. 3 shows a flowchart of a process 300 which may be used for the test cassette extraction 210 of FIG. 2. The process 300 starts with receiving an input image 202, an example of which is shown in FIG. 8A (at the top). In the illustrated embodiment, the input image 202 has a size of 1280×720 pixels, but the skilled reader will understand that the principles explained herein apply to images with other sizes as well. In practice, however, the inventors have found that 1280×720 pixels provides a good starting point for the image processing, because this results in images with enough detail while higher image resolutions do not seem to add much detail for a standard application scenario in which a single test cassette (see, e.g., FIG. 9A at the top) or a modest number of test cassettes is depicted in the input image (e.g., FIG. 9B at the top shows an example input image with 3×4 test cassettes). Other image sizes may be preferred to process images with larger amounts of test cassettes.

The process 300 creates a downscaled image 302, which has a size of 256×144 pixels in the illustrated embodiment. In other words, the input image 202 is downscaled by a factor of 5 in this example. As already explained further above, a downscaling factor of 5 may be particularly feasible if (rotated) bounding boxes are used as object markers, while other downscaling factors, such as 10, may be preferred for other types of image markers, e.g., image masks. Thus, the skilled reader will understand that the principles disclosed herein lend themselves to different kinds of downscaling factors, not only in the process 300 but also in the other processes disclosed herein.

The downscaled image 302 may also be RGB normalized. Normalizing the RGB values of the image is a simple and effective way to make the image processable by a neural network. As the skilled person will know, an RGB color space is an additive color space based on the RGB color model defined by chromaticity coordinates of the red, green, and blue additive primaries, the whitepoint which is usually a standard illuminant, and the transfer function which is also known as the tone response curve (TRC) or gamma. The RGB color model is an additive color model in which the red, green, and blue primary colors of light are added together in various ways to reproduce a broad array of colors. The name of the model comes from the initials of the three additive primary colors, red, green, and blue.

The downscaled image 302 serves as input into a test cassette (TC) segmentation model 304. In the embodiment of FIG. 3, the TC segmentation model 304 is based on a U-Net with 3 (4) levels and 4 (16) initial features. The purpose of the TC segmentation model 304 is to separate the test cassette 100 (TC) from the background (BG) and to create a corresponding first mask 306. In the embodiment of FIG. 3, the mask 306 has a size of 256×144 pixels (matching the size of the downscaled image 302) and is then upscaled to 1280×720 pixels to match the size of the original input image 202. An example of a mask 306 is shown in FIG. 8A (in the middle).

The mask 306, as well as the other masks used elsewhere in certain embodiments (see further below), may be implemented as a binary image with either a zero- or non-zero value for each pixel. Such a binary mask can be searched for a connected component, and a bounding box may be generated based on the connected component. Generally, masking may be implemented, e.g., using pixel multiplication or logical AND, as disclosed in "HIPR—Hypermedia Image Processing Reference" by R. Fisher et al. (J. Wiley & Sons, 1996, page 235; https://www.dsi.unive.it/~atorsell/Hipr.pdf).

In certain embodiments, the process of generating the mask 306 computes the probability that a given pixel belongs to a test cassette. If the probability is above a given threshold, e.g. 80% (or more generally selected from the range of 50 to 99%), the pixel is defined as belonging to a test cassette.

For upscaling a mask, techniques such as nearest neighbor interpolation may be used in certain embodiments of the invention.

The mask 306 applies, in the illustrated embodiment, to classes 0 and 1 (background, test cassette). In certain embodiments, a suitable loss function is binary cross entropy with a threshold for the binary mask of 0.75.

Applying the mask 306 to the original input image 202, as shown in FIG. 8A (at the bottom), allows cutting out an image which contains only the test cassette 100, which cut-out image is referred to as TC image 308 in FIG. 3. An example of a TC image 308 is shown in FIG. 8B (to the left).

In the embodiment of FIG. 3, the generated TC image 308 and/or the mask 306 is subjected to one or more TC sanity checks 310, which may include one or more of (preferably for each connected component obtained from the binary mask):
  area covers at least a minimum amount of pixels, e.g., 10.000 pixels
  ratio height/with depending on number of viewports (e.g., 1.9 for single viewport test cassettes)

In one embodiment, the extract of a presumed test cassette will be discarded if one of the sanity checks 310 fails, because the algorithm did not detect a valid test cassette, and the analysis pipeline will be aborted. The image may be discarded if no test cassette is present. In this case, the next (current) image from the camera stream may be processed.

Viewport Extraction

Figure 4:
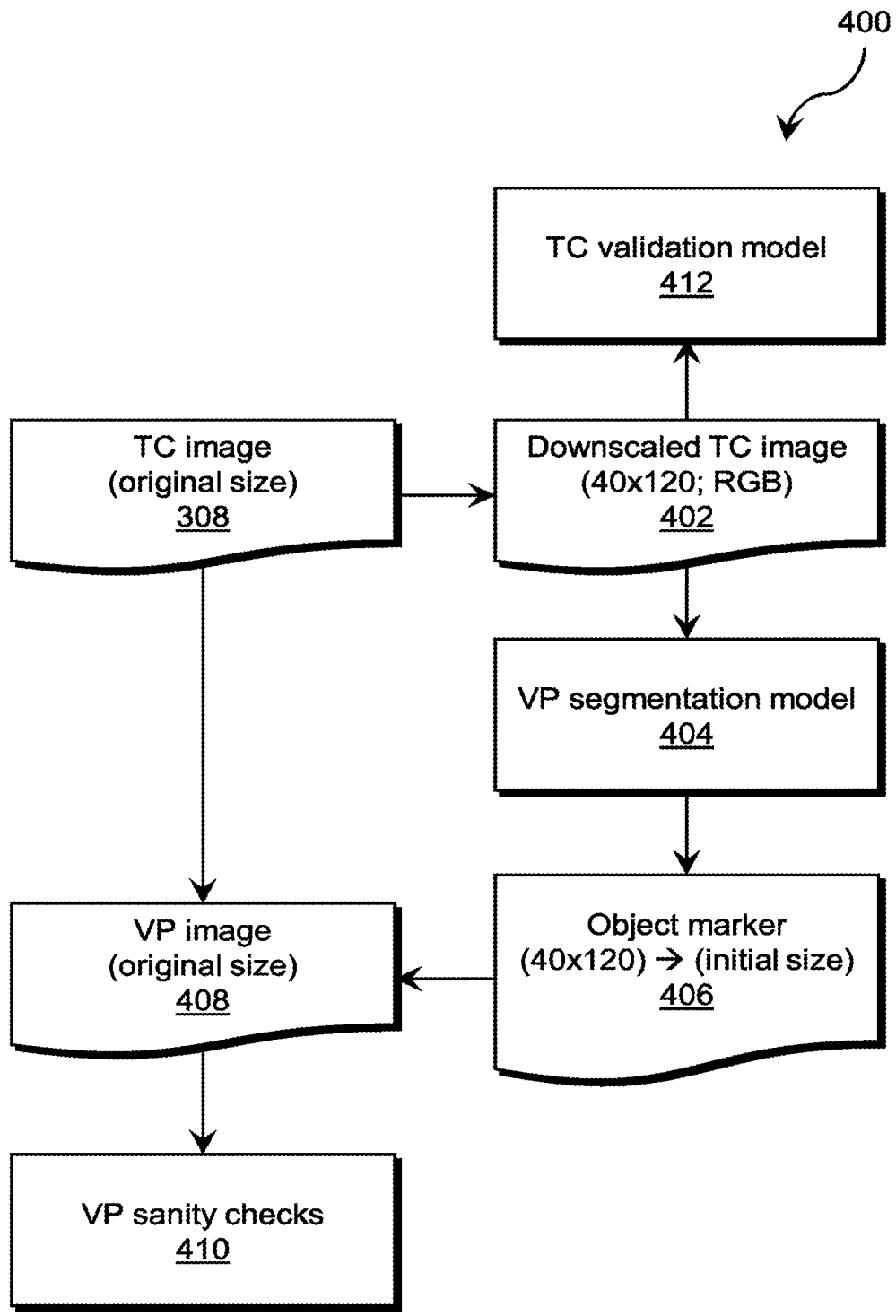
FIG. 4: A flowchart illustrating a viewport extraction process in accordance with embodiments of the invention

FIG. 4 shows a flowchart of a process 400 which may be used for the viewport extraction 212 of FIG. 2. The process 400 starts with receiving a TC image 308, an example of which is shown in FIG. 8B (to the left). The size of the TC image 308 depends on the size of the original image 202 and the position of the test cassette 100 in the original image 202.

The process 400 creates a downscaled TC image 402, which has a size of 40×120 pixels in the illustrated embodiment. The width may depend on the number of viewports 102, apparently, e.g., a multiplex test with two viewports 102 may result in a size of 80×120 pixels, and so on.

The downscaled TC image 402 serves as input into a viewport (VP) segmentation model 404. In the embodiment of FIG. 4, the VP segmentation model 404 is based on a U-Net with 3 levels and 16 (12) initial features. The purpose of the VP segmentation model 404 is to separate the viewport (VP) from the test cassette 100 (TC) and the background (BG) and to create a corresponding second mask 406. In the embodiment of FIG. 4, the mask 406 has a size of 40×120 pixels (matching the size of the downscaled TC image 402) and is then upscaled to the size of the original TC image 308. An example of a mask 406 is shown in FIG. 8B (in the middle).

Accordingly, the mask 406 applies, in the illustrated embodiment, to classes 0-2 (background, test cassette, viewport). In certain embodiments, a suitable loss function is categorical cross entropy where each pixel is assigned to the class having the highest probability.

Applying the mask 406 to the TC image 308, as shown in FIG. 8B (to the right), allows cutting out an image which contains only the viewport 102, which cut-out image is referred to as VP image 408 in FIG. 4. An example of a VP image 408 is shown in FIG. 8C (at the top).

In the embodiment of FIG. 4, the generated VP image 408 and/or the mask 406 is subjected to one or more VP sanity checks 410, which may include one or more of:
  area covers at least a minimum amount of pixels, e.g., 500 pixels
  ratio height/width depending on number of viewports (e.g., 2 for single viewport test cassettes)
  number of connected components, e.g. TC at most three, VP has to match number of viewports of the test cassette
  coverage TC+VP above a predefined threshold, e.g., 70% (or 60%)

Also here, the process may be aborted if one of the sanity checks 410 fails, and repeated using the next image from the camera stream.

Figure 5:
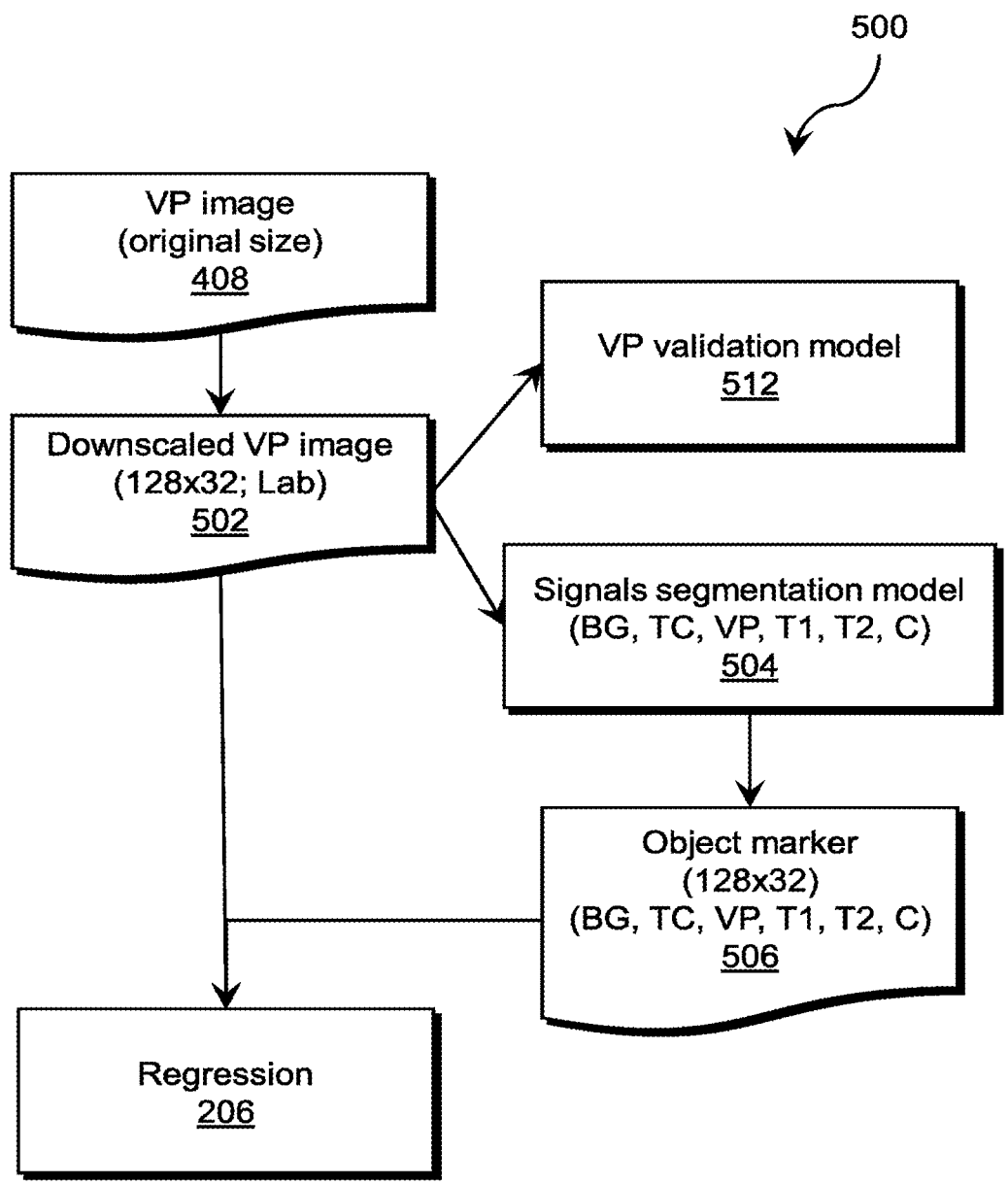
FIG. 5: A flowchart illustrating a signal detection process in accordance with embodiments of the invention

Furthermore, in certain embodiments, two distinct validation models may be used that process each extracted test cassette and viewport, respectively (see the TC validation model 412 in FIG. 4 and the VP validation model 512 in FIG. 5). The validation models may be based on the MobileNetv2 architecture and may check if the presented image is a valid test cassette or a valid viewport (image classification). Alternatively, the validation models may rely on other architectures such as ResNet (K. He et al., Deep residual learning for image recognition. In Proceedings of the IEEE conference on computer vision and pattern recognition, pages 770-778, 2016), ShuffleNet (N. Ma et al., Shufflenet v2: Practical guidelines for efficient cnn architecture design. In Proceedings of the European conference on computer vision (ECCV), pages 116-131, 2018) or SqueenzeNet (F.

Iandola et al., Squeezenet: Alexnet-level accuracy with 50× fewer parameters and, 0.5 mb model size. arXiv preprint arXiv:1602.07360, 2016) as backbone, but these models may become significantly larger and are not designed specifically for mobile usage.

Moreover, the validation models may also determine additional useful supplementary information or metadata, such as the number of viewports, the number of signals and/or the orientation of the image.

More precisely, as shown in FIG. 4, the downscaled TC image 402 is input into a TC validation model 412. Note that in the example of FIG. 4 the downscaled TC image 402 is applied to the VP segmentation model 404 and the TC validation model 412 in parallel, but such parallel processing is not required.

The TC validation model 412 may take as input an image of an extracted test cassette (e.g., scaled to 120×40) and may produce as output one or more of the following:

The probability that the extract of the original image is a test cassette (e.g., loss function: binary cross entropy). The extracted image may be discarded if the probability is below a given threshold, e.g., 50-60%.

Orientation: rotated by, e.g., 180° (e.g., loss function: binary cross entropy). The image may be rotated by 180° if the probability is above, e.g., 50%.

The number of viewports (e.g., 1, 2) (e.g., loss function: categorical cross entropy). The viewport segmentation model 404 may depend on the number of viewports of the test cassette.

The number of signals per LFA (e.g., 1, 2) (e.g., loss function: categorical cross entropy). The viewport signal segmentation model 404 may depend on the number of signal bands (e.g., 2, 3). Depending on the test, it might be better to rely on the test cassette image instead of viewport excerpts to determine the number of signals.

Signal Detection

FIG. 5 shows a flowchart of a process 500 which may be used for the signal detection 214 of FIG. 2. The process 500 starts with receiving a VP image 408, an example of which is shown in FIG. 8C (at the top). The size of the VP image 408 depends on the size of the original image 202 and the position of the viewport 102 within the test cassette 100 in the original image 202.

The process 500 creates a downscaled VP image 502, which has a size of 128×32 pixels in the illustrated embodiment. In other embodiments, different image sizes may be more suitable, such as 80×24 pixels or 60×20 pixels, for example.

In the illustrated embodiment, the downscaled VP image 502 is converted to the Lab color space. The Lab color space, also referred to as CIELAB color space or L*a*b* is a color space which expresses color as three values: L* for perceptual lightness, and a* and b* for the four unique colors of human vision: red, green, blue, and yellow. Operating in the Lab color space may be beneficial in some embodiments because the brightness of the test lines (the L value) resembles the signal values to be evaluated. Therefore, the processing pipeline does not need to learn how to compute the grey value or, respectively, the brightness, from an RGB image. However, it is also possible to operate on RGB images.

The downscaled VP image 502 serves as input into a signals segmentation model 504. In the embodiment of FIG. 5, the signals segmentation model 504 is based on a U-Net with 4 levels and 16 (32) initial features. The model may depend on the number of detected viewport signals. The purpose of the signals segmentation model 504 is to separate the signals 104, 106 (T1, T2, C) from the viewport 102 (VP), the test cassette 100 (TC) and the background (BG) and to create a corresponding third mask 506. In the embodiment of FIG. 5, the mask 506 has a size of 128×32 pixels (matching the size of the downscaled VP image 502). An example of a mask 506 is shown in FIG. 8C (in the middle).

Accordingly, the mask 506 applies, in the illustrated embodiment, to classes 0-5 (background, test cassette, viewport, C, T1, T2). In certain embodiments, a suitable loss function is categorical cross entropy where each pixel is assigned to the class having the highest probability.

In the embodiment of FIG. 5, the generated mask 506 is subjected to one or more sanity checks, which may include one or more of:

number of connected components, e.g., C=1, T1=1, T2≤1 number of pixels per detected signal type, e.g., C, above a predefined threshold, e.g., standard deviation of viewport pixels below a certain threshold, e.g., 10 noticeable color/brightness difference between viewport and C band (i.e., C band should be visible)

As also shown in FIG. 5, the downscaled VP image 502 is input into a VP validation model 512, which may produce one or more of the following outputs:

The probability that the extract is a viewport (e.g., loss function: binary cross entropy).

An extracted image may be discarded if the probability is below, e.g., 80%.

The number of signals (e.g., 1, 2) (e.g., loss function: categorical cross entropy). An image may be discarded if the probability is below, e.g., 50% and/or the number of signals does not match the test.

Prediction of Rotated Bounding Boxes

In certain embodiments, except for the signal detection step 214, the predicted masks 306 and 406 are only used to compute bounding boxes of the respective entities. In other words, instead of relying on masks, i.e., semantic segmentation, as explained further above, certain embodiments comprise a direct prediction of bounding boxes, i.e., object detection.

In this context, a rotated bounding box may be specified by the position of the center (e.g., in x and y coordinates), the height, width and rotational angle.

Directly predicting bounding boxes is particularly useful if multiple instances (e.g., test cassettes) are placed very close to each other such that a clear separation is not visible in masks. Moreover, intermediate processing steps may become obsolete (e.g., finding connected components of masks). On the other hand, a larger image resolution may be beneficial for bounding box prediction and the resulting models may be more computationally expensive.

In certain embodiments, an approach similar to the "you only look once" (YOLO) model family may be employed (see, e.g., Redmon et al., You only look once: Unified, real-time object detection. In Proceedings of the IEEE conference on computer vision and pattern recognition, pages 779-788, 2016; or Redmon and Farhadi, Yolo9000: better, faster, stronger. In Proceedings of the IEEE conference on computer vision and pattern recognition, pages 7263-7271, 2017).

The image may be divided into grid cells for which the model predicts the features of a cell including the probability that a center of a bounding box falls in the grid cell, the probability of the class, center (position within grid cell), height, width (relative to image size), and/or rotational angle (e.g., expressed using trigonometric functions).

Certain embodiments may use a MobileNetv2 or a variant thereof (see, e.g., Sandler et al., Mobilenetv2: Inverted residuals and linear bottlenecks. In Proceedings of the IEEE conference on computer vision and pattern recognition, pages 4510-4520, 2018) as feature extractor, as it is designed for mobile applications.

Figure 9A:
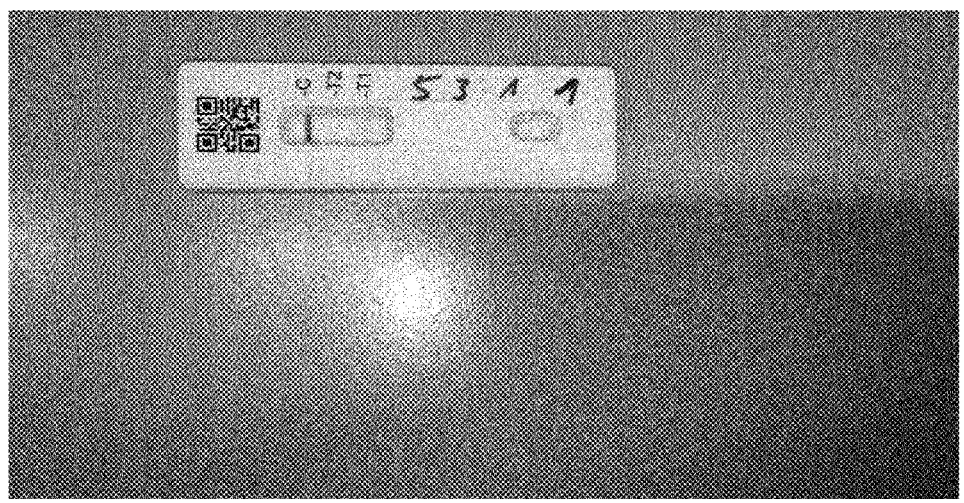
Figure 9A:
Figure 9A:
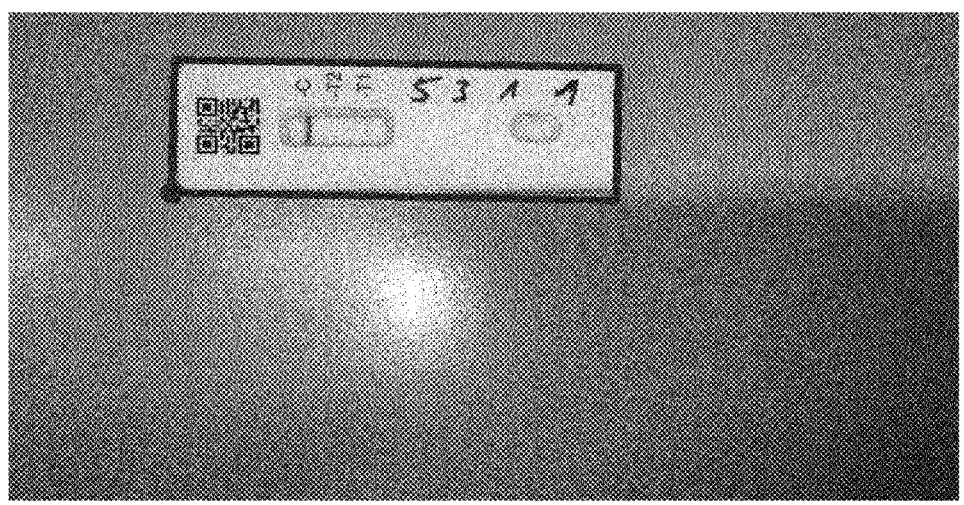
Figure 9B:
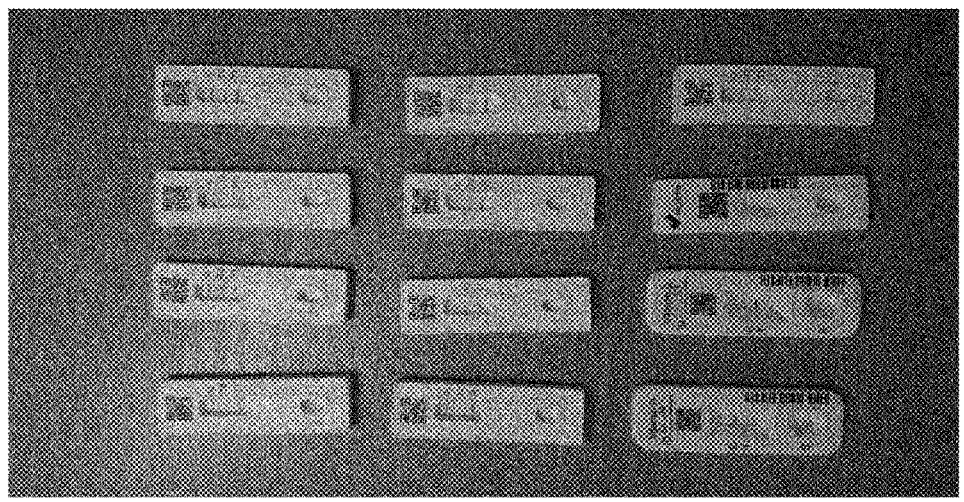
Figure 9B:
Figure 9B:
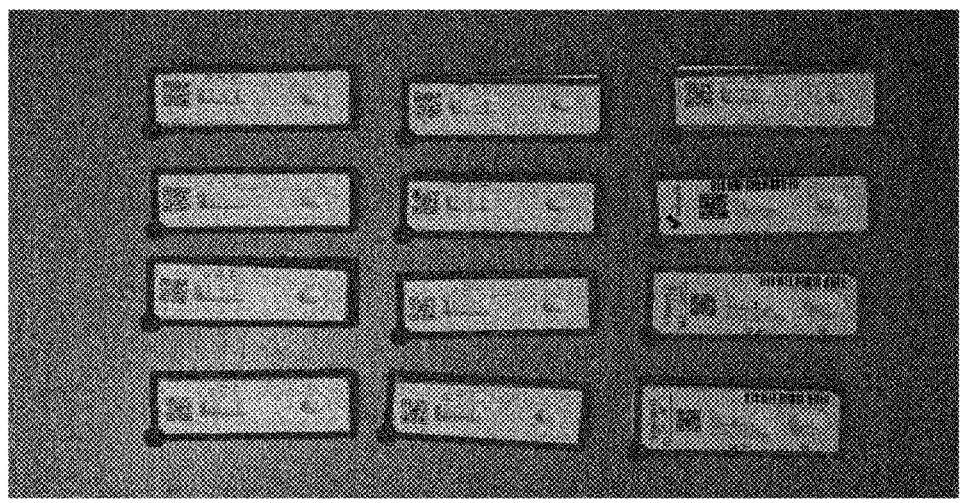

Accordingly, in an embodiment of the invention employing bounding boxes, the test cassette segmentation model 304 may take as input an image 202 of 128×72 pixels, more preferably of 256×144 pixels, and may output rotated bounding boxes around test cassettes 100. For purposes of illustration and comparison with the previously explained embodiment using masks, FIG. 9A shows an exemplary input image 202 with a single test cassette 100 (top), a corresponding mask (middle) and a corresponding bounding box (bottom), and FIG. 9B shows an exemplary input image 202 with twelve test cassettes 100 (top), a corresponding mask (middle) and corresponding bounding boxes (bottom). Suitable sanity checks may comprise checking a minimum size and/or height/width ratio). The viewport segmentation model 404 may take as input an extracted test cassette scaled 40×120, 80×120, etc., depending on the number of viewports, and may output rotated bounding boxes around viewports.

Regression

Figure 6:
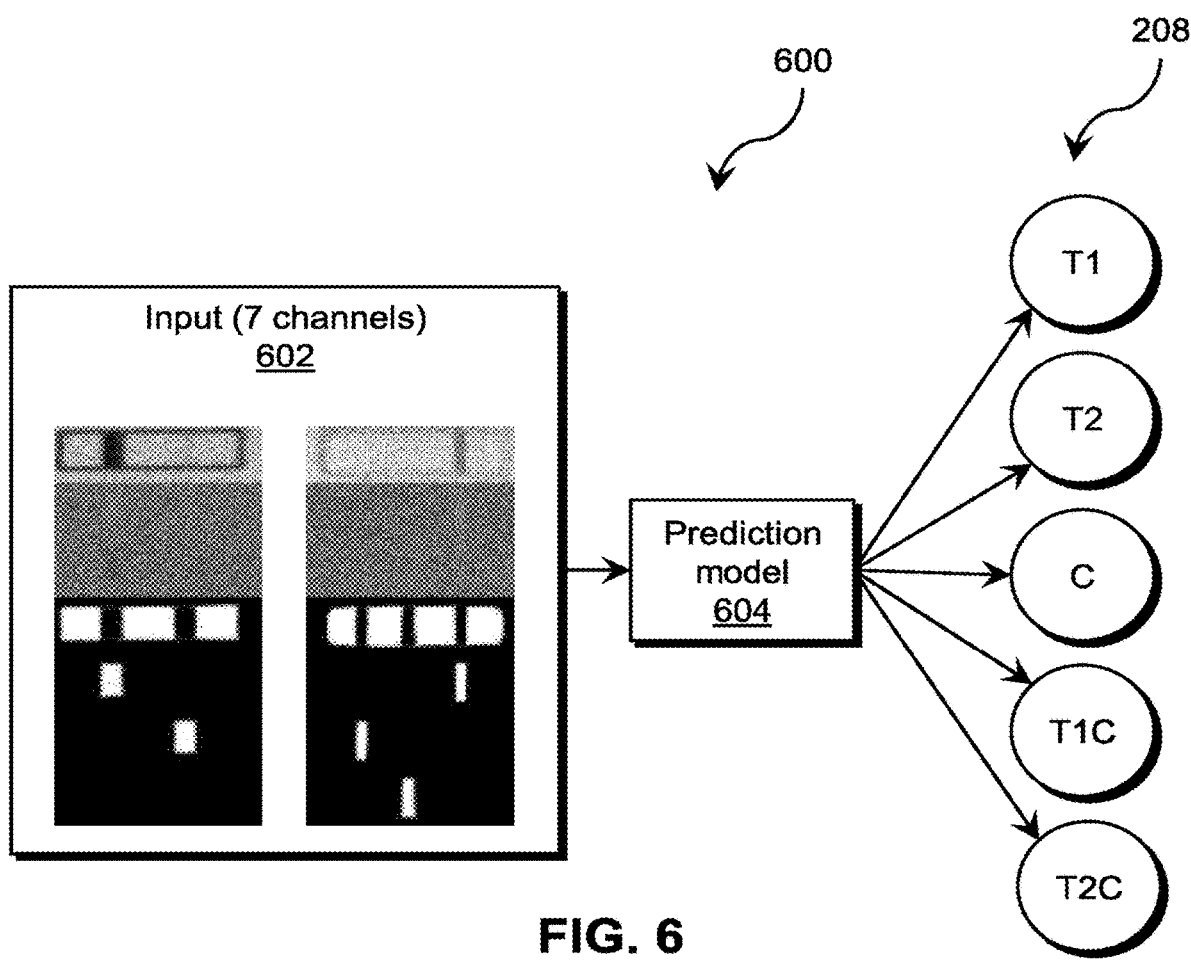
FIG. 6, 7: Schematic illustrations of machine-learning based prediction models in accordance with embodiments of the invention
Figure 7:
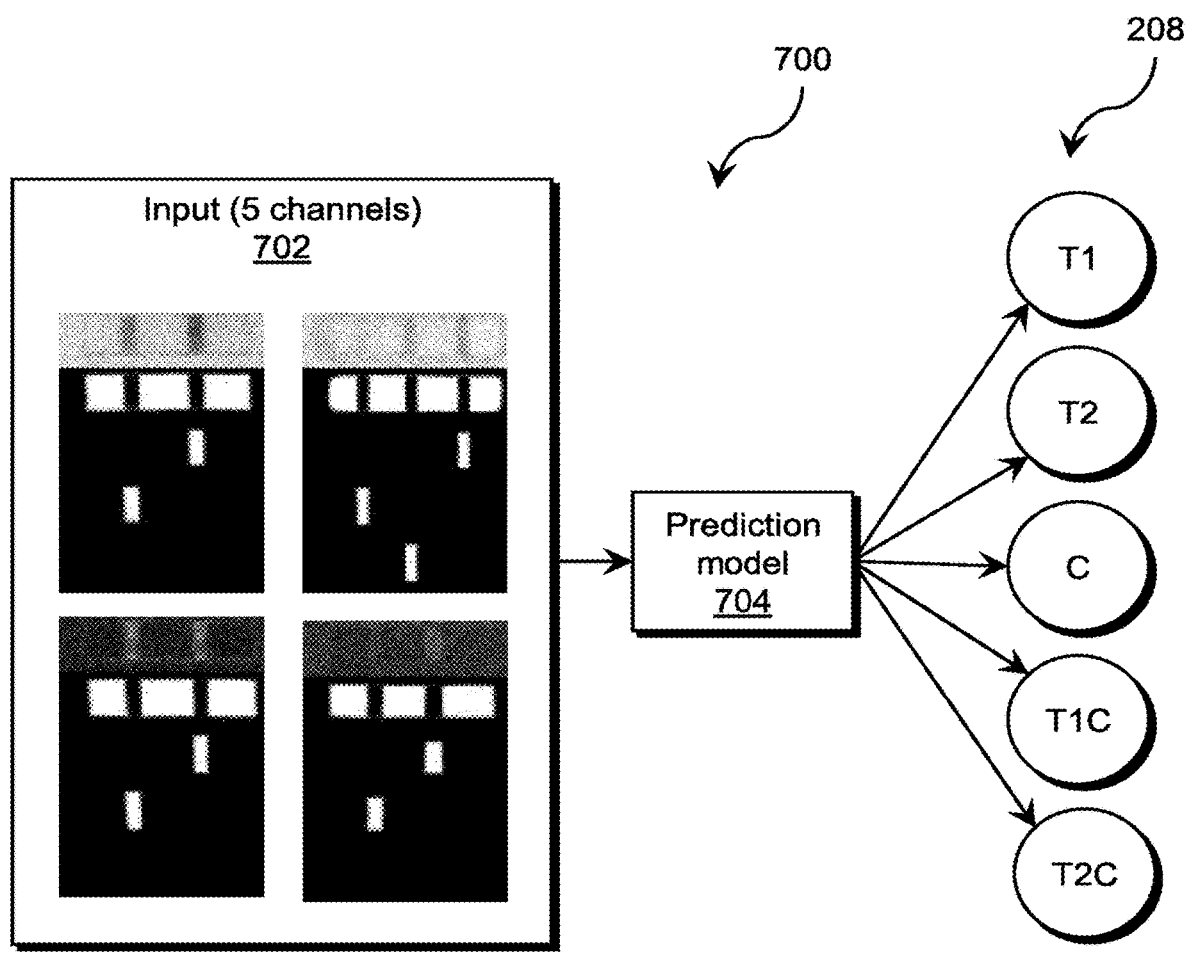

FIGS. 6 and 7 show embodiments of prediction models 604 and 704 which may be used for the regression 206 of FIG. 2. In certain embodiments, the input 602, 702 to the prediction models 604, 704 comprises the cut-out viewport image (i.e., the downscaled viewport image 502) and the mask 506 associated with the bands (also referred to as "test lines" or "signals" herein).

In the illustrated embodiment, the mask 506 defines the probabilities (0.0 to 1.0) for each pixel to represent a certain entity of the viewport (e.g., test lines and background), as will be explained in more detail in the following.

In certain embodiments, the images may be normalized to increase robustness. For example, an RGB version of the viewport image can be normalized based on the segmentation mask. All pixels may be divided by the median value of the viewport pixels (class 2) and consequently clipped at 1. The values of the resulting image may be scaled to the range 0 to 1. In consequence of this transformation, the viewport pixels are very white (i.e., at least 50% of the pixels are exactly white). The resulting image can be converted to the Lab color space.

In the embodiment of FIG. 6, the input 602 has seven channels, including three channels for the image (in Lab colors):
- L (lightness): black to white
- a: green to red
- b: blue to yellow In the embodiment of FIG. 7, the input 702 has five channels, including one channel for the image, namely only the L values.

The values of the first channel may also be 1-L instead of L. As the skilled reader will understand, the L-channel refers to the perceptual lightness from 0 (dark/black) to 1 (bright/white). Since the purpose of embodiments of the invention is to predict the intensity of the bands, it may be practical to invert the values.

In addition, both inputs 602 and 702 include four channels for the segmentation mask 506, which defines a probability of the viewport (VP) and the signals (T1, T2, C). In the illustrated example, these channels represent the probability of each pixel belonging to a certain component of the viewport (viewport 102, C 106, T1 104, T2 104). The skilled reader will understand that the number of channels may differ with the number of signals to be detected.

In both embodiments, the targets of the regression are the signals 208 "T1", "T2", "C", "T1C" and/or "T2C", which enables a direct prediction, as well as an indirect prediction as, e.g., defined by $$\frac{T1}{C} \text{ or } \frac{T2}{C}, \text{ or}$$

$$\frac{\left(T1C + \frac{T1}{C}\right)}{2} \text{ or } \frac{\left(T2C + \frac{T2}{C}\right)}{2}.$$

Note that T2 and T2C are optional, i.e., zero if not present in the test cassette 100 (such as the test cassette 100 shown on the upper left-hand side of FIG. 1A).

In certain embodiments, the regression model 604, 704 is based on a MobileNet, in particular a MobileNetv2 architecture. The person skilled in the art, however, will appreciate that other feature extractors may also be used.

In one particular embodiment, the inputs of the regression model 604, 704 include:
- viewport image: scaled to, e.g., 128×32 (80×24 etc.) (RGB, Lab: all three channels, only the lightness channel (L))
- pixel-accurate probability distribution over relevant classes (e.g. VP, C, T1, T2) (mask 506 generated by the signals segmentation model 504)

The output of the regression model 604, 704 is in this embodiment:
- test result 208, comprising values for C, T1, T2, T1C and/or T2C (e.g., loss function: mean squared error)

The machine-learning models used in embodiments of the invention can be trained with training datasets, e.g., comprising labelled digital images of test cassettes, and using any of several suitable training methods, as known to the person skilled in the art.

System Architectures

Figure 1B:
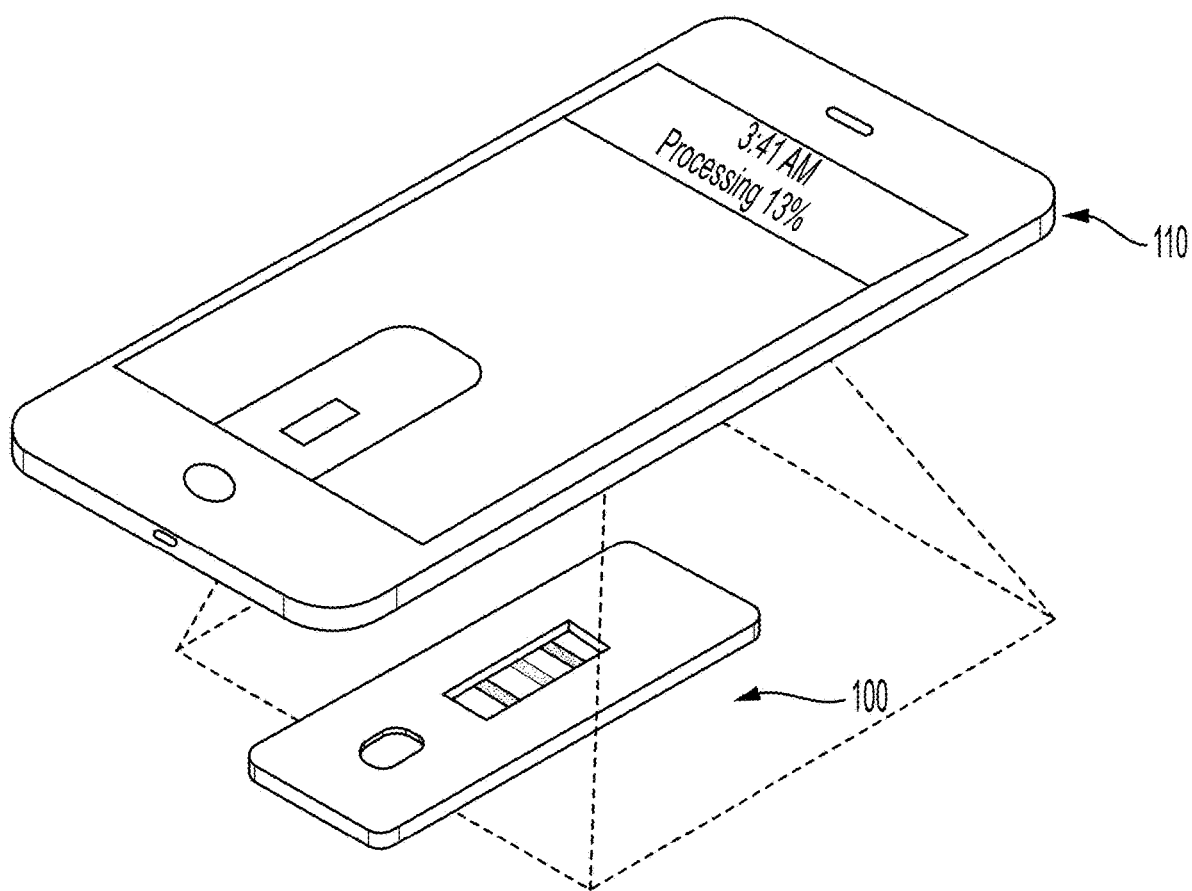
FIG. 1B: A schematic illustration of an automated LFA evaluation using a smartphone

In the above-disclosed embodiments, the processing is performed to a large extent, and in some embodiment even entirely, on a mobile electronic device, e.g., the smartphone 110 shown in FIG. 1B. This is possible because embodiments of the invention include very small models thanks to the disclosed techniques, as explained already above. Such an embodiment is advantageous because the processing happens on one single device. If even the input images are taken with the device, there is no need for any network communication and data transfer at all, so that the entire process can be performed locally without any network connection.

Figure 10:
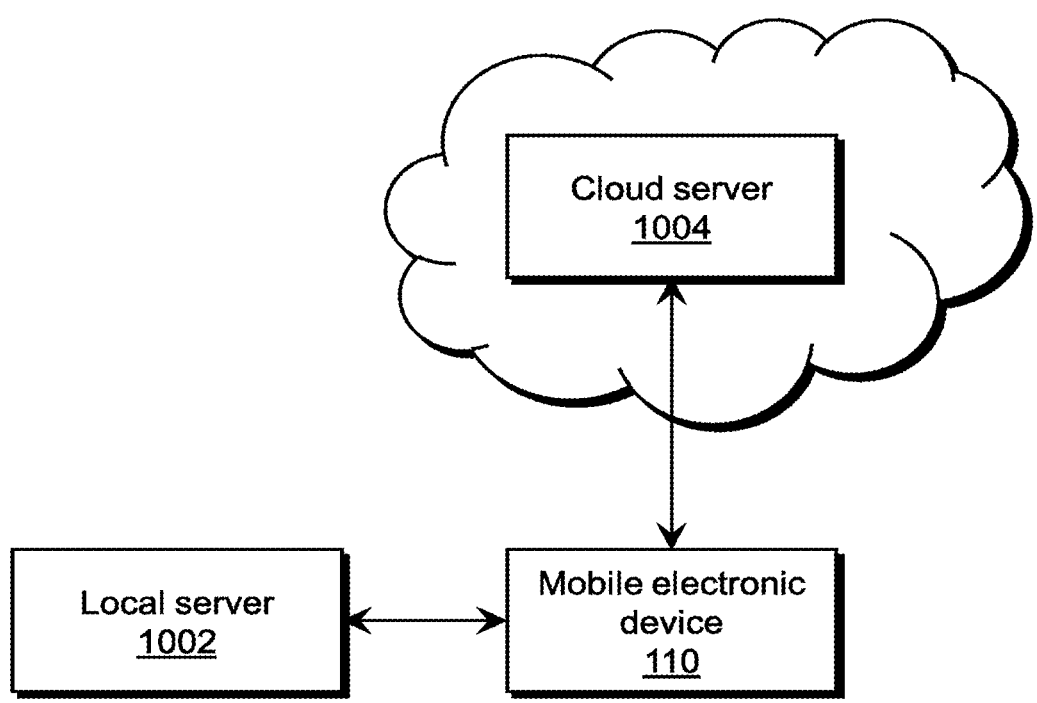
FIG. 10: A schematic illustration of a distributed system architecture in accordance with embodiments of the invention

However, it is also possible to perform at least some of the steps external to the smartphone 110. For example, FIG. 10 shows a local server 1002, which may be located near the smartphone 110 or at least operated by the same entity, and a remote server 1004 (labelled "cloud server" in FIG. 10), each of which may be employed to perform some of the steps disclosed herein.

General Remarks

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some or all of the method steps may be executed by (or using) a hardware apparatus, such as a processor, a microprocessor, a programmable computer or an electronic circuit. Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments of the invention provide a data carrier having electronically readable control signals, which are capable of cooperating with a programmable computer system, such that one of the methods described herein is performed.

Generally, embodiments of the invention can be implemented as a computer program (product) with a program code, the program code being operative for performing one of the methods when the computer program product runs on a computer. The program code may, for example, be stored on a machine-readable carrier. Other embodiments comprise the computer program for performing one of the methods described herein, stored on a machine-readable carrier. In other words, an embodiment of the present invention is, therefore, a computer program having a program code for performing one of the methods described herein, when the computer program runs on a computer.

A further embodiment of the invention provides a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention provides a data stream or a sequence of signals representing the computer program for performing one of the methods described herein. The data stream or the sequence of signals may, for example, be configured to be transferred via a data communication connection, for example, via the internet.

A further embodiment of the invention provides a processing means, for example, a computer or a programmable logic device, configured to, or adapted to, perform one of the methods described herein.

A further embodiment of the invention provides a computer having installed thereon the computer program for performing one of the methods described herein.

A further embodiment of the invention provides an apparatus or a system configured to transfer (e.g., electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Certain embodiments of the invention may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g., sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e., each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g., a classification algorithm, a regression algorithm or a similarity learning algorithm). Classification algorithms may be used when the outputs are restricted to a limited set of values (categorical variables), i.e., the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters. Reinforcement learning is a third group of machine-learning algorithms that may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a preprocessing step before performing classification or predictions. Feature learning may be based on principal components analysis or cluster analysis, for example.

In some examples, anomaly detection (i.e., outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g., a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g., based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g., of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e., support vector networks) are supervised learning models with associated learning algorithms that may be used to analyze data (e.g., in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

The invention claimed is:

1. A computer-implemented method for lateral flow test evaluation, wherein the method comprises the following steps:
    obtaining a digital image (202) that depicts at least one test cassette (100), wherein the test cassette (100) comprises at least one viewport (102) and wherein the viewport (102) comprises at least one test indicator (104);
    performing an image segmentation step (204) to recognize at least one test indicator (104) depicted in the digital image (202); and
    performing an evaluation step (206) for producing at least one evaluation result (208) based, at least in part, on the recognized at least one test indicator (104);
    wherein the image segmentation step (204) comprises generating at least one object marker (306, 406, 506), in particular at least one mask and/or bounding box, based on a downscaled version of the obtained digital image (202) and applying the at least one object marker (306, 406, 506) to the obtained digital image (202) or to a part thereof, wherein the image segmentation step (204) comprises:
    a test cassette extraction step (210), comprising:
        generating a downscaled digital image (302) from the obtained digital image (202);

generating, based on the downscaled digital image (302) and using at least one segmentation machine-learning model (304), a first object marker (306) associated with a test cassette (100) depicted in the obtained digital image (202), preferably one first object marker (306) for each test cassette (100) depicted in the obtained digital image (202); and extracting, using the first object marker (306), a test cassette image (308) from the obtained digital image (202) preferably one test cassette image (308) for each test cassette (100) depicted in the obtained digital image (202);

a viewport extraction step (212), comprising:
generating a downscaled test cassette image (402) from the test cassette image (308);
generating, based on the downscaled test cassette image (402) and using at least one segmentation machine-learning model (404), a second object marker (406) associated with a viewport (102) depicted in the obtained digital image (202); and
extracting, using the second object marker (406), a viewport image (408) from the test cassette image (308); and a signal detection step (214) to recognize at least one test indicator (104) comprising:
generating a downscaled viewport image (502) from the viewport image (408); and
generating, based on the downscaled viewport image (502) and using at least one segmentation machine-learning model (504), a third object marker (506) associated with at least one test indicator (104) depicted in the obtained digital image (202);
wherein generating the at least one object marker (306, 406, 506) comprises processing the respective downscaled image with a separate segmentation machine-learning model (304, 404, 504) for each object marker (306, 406, 506), and
wherein the evaluation step (206) is based at least in part on the third object marker (506) and on the downscaled viewport image (502) comprising the at least one test indicator (104).

2. The method according to claim 1, wherein the evaluation step (206) comprises:
using a prediction machine-learning model (604, 704) to generate at least one value for the at least one test indicator (104), and optionally, a control indicator (106) of the at least one test cassette (100) to enable an accurate quantitative evaluation of the lateral flow test; and/or
displaying the at least one evaluation result (208) on a display of an electronic device.

3. The method according to claim 1, wherein the downscaled digital image (302) is downscaled by a factor selected from the range of 5 to 15, more preferably from the range of 8 to 12, most preferably by a factor of 10 relative to the obtained digital image (202), or by a factor selected from the range of 2 to 8, more preferably from the range of 4 to 6, most preferably by a factor of 5 relative to the obtained digital image (202); and/or
wherein the size of the obtained digital image (202) is 1280×720 pixels and the size of the downscaled digital image (302) is 128×72 pixels or 256×144 pixels; and/or
wherein the size of the downscaled test cassette image (402) is 40×120 pixels or 80×240 pixels, or wherein the height is 120 pixels and the width is a multiple of 40 pixels depending on the number of viewports of the test cassette; and/or
wherein the size of the downscaled viewport image (502) is 80×24 pixels or 160×48 pixels or 128×32 pixels.

4. The method according to claim 1, wherein the downscaled digital image (302) adheres to an RGB color model, the downscaled test cassette image (402) adheres to an RGB color model and/or the downscaled viewport image (502) adheres to a Lab color model.

5. The method according to claim 1, which comprises at least one of the following further steps:
performing at least one sanity check (310) on the extracted test cassette image (308);
performing at least one sanity check (410) on the extracted viewport image (408);
validating the downscaled test cassette image (402), preferably using a test cassette validation machine-learning model (412);
validating the downscaled viewport image (502), preferably using a viewport validation machine-learning model (512).

6. The method according to claim 1, wherein the first segmentation machine-learning model (304), the second segmentation machine-learning model (404), the third segmentation machine-learning model (504), the prediction machine-learning model (604, 704), the test cassette validation machine-learning model (412) and/or the viewport validation machine-learning model (512) comprises an artificial neural network, in particular a convolutional neural network, CNN.

7. The method according to claim 1, wherein the first segmentation machine-learning model (304), the second segmentation machine-learning model (404) and the third segmentation machine-learning model (504) is based on a U-Net or a Yolo model and the prediction machine-learning model (604, 704), the test cassette validation machine-learning model (412) and/or the viewport validation machine-learning model (512) is based on a MobileNetv2.

8. The method according to claim 1, being performed, at least in part, by a mobile electronic device (110), preferably a handheld device, in particular a handheld consumer device such as a smartphone or tablet computer.

9. A data processing apparatus, in particular a mobile electronic device (110) or a server computing system, comprising means for carrying out the method of claim 1.

10. A computer program comprising instructions which, when the program is executed by a computer, cause the computer to carry out the method of claim 1.

* * * * *